United States Patent

Maurer et al.

[11] 4,113,860
[45] Sep. 12, 1978

[54] O-ALKYL-O-[4-ALKYLPYRIMIDIN(2)YL]-(THIONO)-(THIOL) PHOSPHORIC (PHOSPHONIC) ACID ESTERS AND INSECTICIDAL, ACARICIDAL AND NEMATOCIDAL COMPOSITIONS CONTAINING THEM

[75] Inventors: Fritz Maurer; Hans-Jochem Riebel, both of Wuppertal; Bernhard Homeyer, Leverkusen; Wolfgang Behrenz, Overath-Steinenbrueck; Ingeborg Hammann, Cologne; Wilhelm Stendel, Wuppertal, all of Germany

[73] Assignee: Bayer Aktiengesellschaft, Leverkusen, Germany

[21] Appl. No.: 645,128

[22] Filed: Dec. 29, 1975

[30] Foreign Application Priority Data

Jan. 17, 1975 [DE] Fed. Rep. of Germany ....... 2501769

[51] Int. Cl.² .......................... A01N 9/36; C07F 9/65
[52] U.S. Cl. .................................. 424/200; 544/243; 544/318
[58] Field of Search ............... 260/251 P; 424/200

[56] References Cited

U.S. PATENT DOCUMENTS

| | | | |
|---|---|---|---|
| 2,754,243 | 7/1956 | Gysin et al. | 260/251 P X |
| 3,328,405 | 6/1967 | Simone et al. | 260/251 P X |
| 3,741,968 | 6/1973 | Haubein | 260/251 P |
| 3,951,975 | 4/1976 | Hofer et al. | 260/251 P |
| 4,014,996 | 3/1977 | Maurer et al. | 424/200 |
| 4,053,594 | 10/1977 | Riebel et al. | 424/200 |

FOREIGN PATENT DOCUMENTS

| | | | |
|---|---|---|---|
| 1,939,821 | 2/1970 | Fed. Rep. of Germany | 260/251 P |
| 2,144,392 | 8/1973 | Fed. Rep. of Germany | 260/251 P |
| 922,378 | 3/1963 | United Kingdom | 260/251 P |

OTHER PUBLICATIONS

Hadaway et al., Bull. World Health Organ, 33(1), pp. 129-140 (1965).
Hadaway et al., Chemical Abstracts, 63 18,961d (1965).

Primary Examiner—Donald G. Daus
Assistant Examiner—Diana G. Rivers
Attorney, Agent, or Firm—Burgess, Dinklage & Sprung

[57] ABSTRACT

O-Alkyl-O-[4-alkylpyrimidin(2)yl]-(thiono)-(thiol) phosphoric (phosphonic) acid esters of the formula

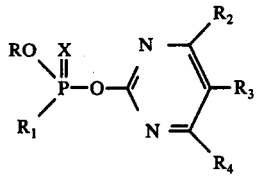

in which
R is alkyl with 1 to 9 carbon atoms,
$R_1$ is alkyl, alkoxy or alkylmercapto each with 1 to 6 carbon atoms, or phenyl,
$R_2$ is alkyl with 1 to 6 carbon atoms,
$R_3$ is hydrogen or halogen,
$R_4$ is halogen, thiocyanato or alkoxy, alkylmercapto or alkoxycarbonyl with 1 to 4 carbon atoms in each radical, and
X is oxygen or sulfur, which possess insecticidal, acaricidal and nematocidal properties.

10 Claims, No Drawings

O-ALKYL-O-[4-ALKYLPYRIMIDIN(2)yl]-(THIONO)-(THIOL) PHOSPHORIC (PHOSPHONIC) ACID ESTERS AND INSECTICIDAL, ACARICIDAL AND NEMATOCIDAL COMPOSITIONS CONTAINING THEM

It is known from U.S. Pat. No. 3,741,968 and German Offenlegungsschrift No. 2,144,392 that pyrimidinyl(thiono)phosphoric acid esters and ester-amides, for example O,O-dimethyl-(Compound A) or O,O-diethyl-O-pyrimidin(2)ylthionophosphoric acid ester (Compound B), O,O-diethyl-O-[2,4-dimethyl-5-methylthiopyrimidin(6)yl]-phosphoric acid ester (Compound C) or -thionophosphoric acid ester (Compound D) or O-methyl-O-[2,4-dimethyl-5-methylthiopyrimidin(6)yl]-N-isopropylthionophosphoric acid ester-amide (Compound E), possess insecticidal and acaricidal properties.

The present invention provides as new compounds, the substituted pyrimidinyl(thiono)-(thiol)phosphoric(phosphonic) acid esters of the general formula

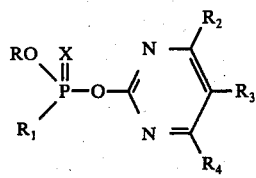

(I)

in which
R is alkyl with 1 to 9 carbon atoms,
$R_1$ is alkyl, alkoxy or alkylmercapto each with 1 to 6 carbon atoms, or phenyl,
$R_2$ is alkyl with 1 to 6 carbon atoms,
$R_3$ is hydrogen or halogen,
$R_4$ is halogen, thiocyanato or alkoxy, alkylmercapto or alkoxycarbonyl with 1 to 4 carbon atoms in each radical, and
X is oxygen or sulfur.

Surprisingly, the substituted pyrimidinyl(thiono)-(thiol)phosphoric(phosphonic) acid esters according to the invention show a better leaf-insecticidal and soil-insecticidal, acaricidal and nematocidal action than the corresponding compounds of analogous structure and of the same type of action previously known from the state of the art. The products according to the present invention thus represent a genuine enrichment of the art.

Preferably, R is straight-chain or branched alkyl with 1 to 4 carbon atoms, $R_1$ is alkyl, alkoxy or alkylmercapto each with 1 to 4 carbon atoms, or phenyl, $R_2$ is straight-chain or branched alkyl with 1 to 4 carbon atoms, $R_3$ is hydrogen, chlorine or bromine, and $R_4$ is chlorine, bromine or thiocyanato, or alkoxy, alkylmercapto or alkoxycarbonyl with 1 to 3 carbon atoms in each alkyl radical.

The present invention also provides a process for the preparation of a pyrimidinyl(thiono)-(thiol)phosphoric(phosphonic) acid ester of the formula (I), in which a (thiono)(thiol)phosphoric(phosphonic) acid ester halide of the general formula

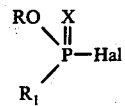

(II)

in which
X, R and $R_1$ have the above-mentioned meanings, and
Hal is halogen, preferably chlorine,
is reacted with a 2-hydroxypyrimidine derivative of the general formula

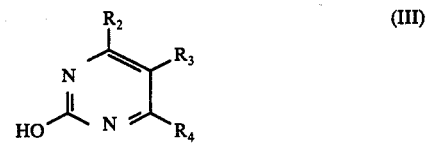

(III)

in which
$R_2$, $R_3$ and $R_4$ have the above-mentioned meanings, the 2-hydroxypyrimidine derivative being employed as such, or as its hydrochloride, in the presence of an acid acceptor, or in the form of an alkali metal salt, alkaline earth metal salt or ammonium salt thereof.

If, for example, O-propyl-thionoethanephosphonic acid ester chloride and 2-hydroxy-4-methyl-6-methoxypyrimidine are used as starting materials, the course of the reaction can be represented by the following equation:

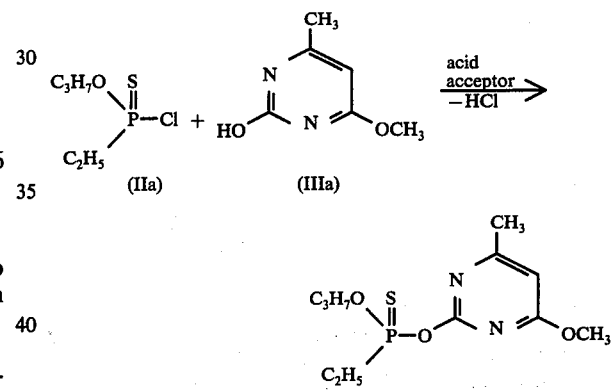

The (thiono)(thiol)phosphoric(phosphonic) acid ester halides (II) to be used as starting materials are known from the literature and can be prepared in accordance with generally customary processes.

The following may be mentioned as examples thereof: O,O-dimethyl-, O,O-diethyl-, O,O-di-n-propyl-, O,O-di-isopropyl-, O,O-di-n-butyl-, O,O-di-isobutyl, O,O-di-sec.-butyl and O,O-di-tert.-butyl-phosphoric acid ester chlorides and the corresponding thiono analogues; O-ethyl, O-n-propyl-, O-isopropyl-, O-n-butyl-, O-isobutyl-, O-sec.-butyl-, O-tert.-butyl-, O-n-pentyl-, O-n-hexyl-, O-n-heptyl-, O-n-octyl and O-n-nonyl-O-methyl- and -O-ethyl-phosphoric acid ester chlorides and the corresponding thiono analogues; O-methyl-, O-ethyl-, O-n-propyl-, O-isopropyl-, O-n-butyl-, O-sec.-butyl-, O-isobutyl- and O-tert.-butyl-methane-, -ethane-, -n-propane-, -iso-propane-, -butane- and -benzene- phosphonic acid ester chlorides and the corresponding thiono analogues; and O,S-dimethyl-, O,S-diethyl-, O,S-di-n-propyl-, O,S-di-isopropyl-, O,S-di-n-butyl-, O,S-di-isobutyl-, O,S-di-sec.-butyl-, O,S-di-tert.-butyl-, O-methyl-S-ethyl-, O-ethyl-S-methyl-, O-ethyl-S-n-propyl- and O-ethyl-S-iso-propylthiolphosphoric acid ester chloride and the corresponding thiono analogues.

The 2-hydroxypyrimidine derivatives (III), some of which are new, can be prepared according to methods known from the literature, for example (a) by reacting a 1,3-diketone with urea in alcoholic solution in the presence of hydrochloric acid, in accordance with the following equation:

$R_2-CO-CH_2-CO-CO-OAlkyl + NH_2-CO-NH_2$ $$\xrightarrow[-2 \times H_2O]{\text{concentrated hydrochloric acid, ethanol}}$$

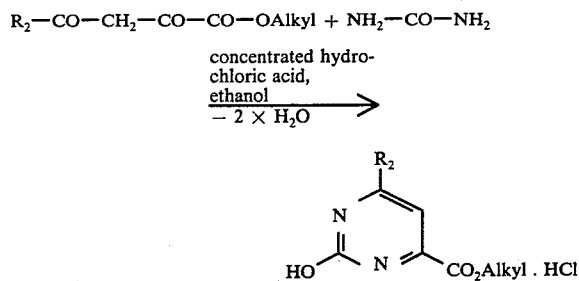

wherein $R_2$ has the above-mentioned meaning, or (b) by converting a 2-methylsulfonylpyrimidine derivative, by means of potassium hydroxide in acetone/water, into a 2-hydroxypyrimidine derivative according to the following equation:

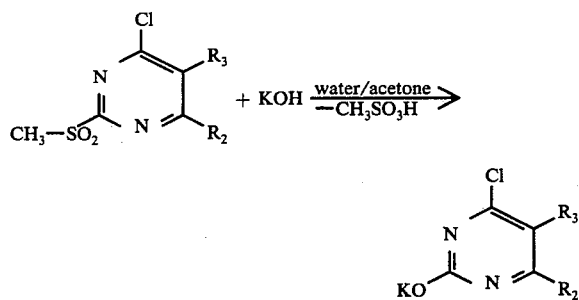

wherein $R_2$ and $R_3$ have the above-mentioned meanings, or (c) by reacting a 2-hydroxy-4-chloropyrimidine derivative with sodium methylate, sodium methylmercaptide or ammonium thiocyanate in dimethylformamide as the solvent, in accordance with the following equations:

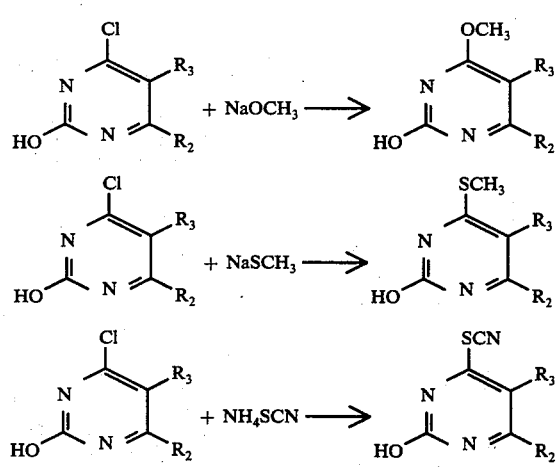

wherein $R_2$ and $R_3$ have the above-mentioned meanings.

The following may be mentioned as examples of the 2-hydroxypyrimidine derivatives (III) to be reacted in accordance with the process: 2-hydroxy-4-methyl-6-bromopyrimidine, 2-hydroxy-4-ethyl-6-bromopyrimidine, 2-hydroxy-4-methyl-5-chloro-6-bromopyrimidine, 2-hydroxy-4-ethyl-5-chloro-6-bromopyrimidine, 2-hydroxy-4-methyl-5-bromo-6-methoxypyrimidine, 2-hydroxy-4-methyl-5-bromo-6-methylmercaptopyrimidine, 2-hydroxy-4-methyl-5,6-dibromopyrimidine, 2-hydroxy-4-methyl-6-carbomethoxypyrimidine, 2-hydroxy-4-methyl-6-carbethoxypyrimidine, 2-hydroxy-4-methyl-6-carboisopropoxypyrimidine, 2-hydroxy-4-tert.-butyl-5-chloro(or bromo)-6-carbomethoxypyrimidine, 2-hydroxy-4-tert.-butyl-5-chloro (or bromo)-6-carbethoxypyrimidine, 2-hydroxy-4-tert.-butyl-5-chloro(or bromo)-6-carboisopropoxypyrimidine, 2-hydroxy-4-methyl-5-chloro(or bromo)-6-carbomethoxypyrimidine, 2-hydroxy-4-methyl-5-chloro(or bromo)-6-carbethoxypyrimidine and 2-hydroxy-4-methyl-5-chloro(or bromo)-6-carboisopropoxypyrimidine.

The process for the preparation of the compounds according to the invention is preferably carried out in the presence of a suitable solvent or diluent. Practically all inert organic solvents can be used for this purpose, especially aliphatic and aromatic optionally chlorinated hydrocarbons, such as benzene, toluene, xylene, benzine, methylene cloride, chloroform, carbon tetrachloride and chlorobenzene; ethers, for example diethyl ether, dibutyl ether and dioxane, ketones, for example acetone, methyl ethyl ketone, methyl isopropyl ketone and methyl isobutyl ketone; and nitroles, such as acetonitrile and propionitrile.

All customary acid-binding agents can be used as the acid acceptors. Alkali metal carbonates and alkali metal alcoholates, such as sodium carbonate and potassium carbonate or potassium tert.-butylate, have proved particularly suitable, as have aliphatic, aromatic or heterocyclic amines, for example triethylamine, trimethylamine, dimethylaniline, dimethylbenzylamine and pyridine.

The reaction temperature can be varied within a fairly wide range. In general, the reaction is carried out at between 0° and 120° C, preferably at 40° to 65° C.

In general, the reaction is allowed to take place under normal pressure.

To carry out the process, the starting components are in general employed in the equimolar ratio. An excess of one or the other component produces no significant advantages. In most cases, the hydrochloride, the sodium salt or the free base of the 2-hydroxypyrimidine derivatives is introduced into one of the stated solvents or diluents, if appropriate together with the acid acceptor, and the ester halide is added dropwise. After heating for one or more hours at the stated temperatures, the reaction mixture is poured into an organic solvent, for example toluene, and is worked up in the usual manner, for example by separating off the organic phase, washing and drying it and distilling off the solvent.

The new compounds are obtained in the form of oils which cannot be distilled without decomposition but are freed from the last volatile constituents by so-called "slight distillation", that is to say by prolonged heating under reduced pressure to moderately elevated temperatures, and are purified in this way. They are characterized by the refractive index.

As has already been mentioned, the substituted pyrimidinyl(thiono)(thiol)phosphoric(phosphonic) acid esters according to the invention are distinguished by an excellent insecticidal, acaricidal and nematocidal activity. They are active not only against plant pests, pests harmful to health and pests of stored products, but also, in the veterinary medicine field, against animal parasites (ectoparasites), such as parasitic fly larvae. They couple a low phytotoxicity with a good action against both sucking and biting insects and against mites.

For this reason, the compounds according to the invention can be employed successfully as pesticides in plant protection, the hygiene field, the field of protection of stored products and the veterinary field.

The active compounds according to the invention are well tolerated by plants and have a favorable level of toxicity to warm-blooded animals, and can be used for combating all or individual stages of development, including the pre-embryonic, normally sensitive and resistant, stages of development of insects, acarids or nematodes, where these are known as pests in agriculture, in forestry, in the protection of stored products and materials, and in hygiene.

When used against pests harmful to health and pests of stored products, the active compounds are distinguished by an excellent residual action on wood and clay, as well as a good stability to alkali on limed substrates.

The economically important pests in agriculture and forestry, as well as pests of stored products, pests destructive of materials and pests harmful to health, include: from the order of the Isopoda, for example, *Oniscus asellus, Armadillidium vulgare* and *Porcellio scaber;* from the order of the Diplopoda, for example, *Blaniulus guttulatus;* from the order of the Chilopoda, for example, *Geophilus carpophagus* and *Scutigera* spec.; from the order of the Symphyla, for example, *Scutigerella immaculata;* from the order of the Arachnida, for example, *Scorpio maurus* and *Latrodectus mactans;* from the order of the Acarina, for example, *Acarus siro, Argas reflexus, Ornithodoros moubata, Dermanyssus gallinae, Eriophyes ribis, Phyllocoptruta oleivora, Boophilus microplus, Ripicephalus evertsi, Sarcoptes scabiei, Tarsonemus* spec., *Bryobia praetiosa, Panonychus citri, Panonychus ulmi, Tetranychus tumidus* and *Tetranychus urticae; from the order of the Thysanura, for example, Lepisma saccharina;* from the order of the Collembola, for example, *Onychiurus armatus;* from the order of the Orthoptera, for example, *Blatta orientalis, Periplaneta americana, Leucophaea maderae, Blattella germanica, Acheta domesticus, Gryllotalpha* spec., *Locusta migratoria migratorioides, Melanoplus differentialis* and *Schistocerca gregaria; from the order of the Dermaptera, for example, Forficula auricularia;* from the order of the Isoptera, for example, *Reticulitermes* spec.; from the order of the Anoplura, for example, *Phylloxera vastatrix, Pemphigus* spec. and *Pediculus humanus corporis;* from the order of the Thysanoptera, for example, Hercinothrips *femoralis* and *Thrips tabaci;* from the order of the Heteroptera, for example, *Eurygaster* spec., *Dysdercus intermedius, Piesma quadrata, Cimex lectularis, Rhodnius prolixus* and *Triatoma spec.; from the order of the Homoptera, for example, Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae, Myzus cerasi, Myzus persicae, Phorodon humuli, Rhopalosiphum padi, Empoasca* spec. *Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus* spec. and *psylla* spec.; from the order of the Lepidoptera, for example, *Pectinophora gossypiella, Bupalus piniarius, Chemiatobia brumata, Lithocolletis blancardella, Hyponomeuta padella, Plutella maculipennis, Malacosoma neustria, Euproctis chrysorrhoea, Lymantria* spec., *Bucculatrix thurberiella, Phyllocnistis citrella, Agrotis spec., Euxoa spec., Feltia spec., Earias insulana, Heliothis spec., Laphygma exigua, Mamestra brassicae, Panolis flammea, Prodenia litura, Spodoptera* spec., *Trichoplusia ni, Carpocapsa pomonella, Pieris* spec., *Chilo* spec., *Pyrausta nubilalis, Ephestia kühniella, Galleria mellonella, Cacoecia podana, Capua reticulana, Choristoneura fumiferana, Clysia ambiguella, Homona magnanima* and *Tortrix viridana;* from the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica* spec., *Psylliodes chrysocephala, Epilachna varivestis, Atomaria* spec., *Orzaephilus surinamensis, Anthonomus* spec., *Sitophilus* spec., *Otiorrhynchus sulcatus, Cosmopolites sordidus, Ceuthorrhynchus assimilis, Hypera postica, Dermestes* spec., *Trogoderma* spec., *Anthrenus* spec., *Attagenus* spec., *Lyctus* spec., *Mleigethes aeneus, Ptinus* spec., *Niptus holoeucus, Gibbium psylloides, Tribolium* spec., *Tenebrio molitor, Agriotes* spec., *Conoderus* spec., *Melolontha melolontha, Amphimallus solstitialis* and *Costelytra zealandica;* from the order of the Hymenoptera, for example, *Diprion* spec. *Hoplocampa* spec., *Lasius* spec., *monomorium pharaonis* and *Vespa* spec.; from the order of the Diptera, for example, *Aëdes* spec., *Anopheles* spec., *Culex* spec., *Drosophila melanogaster Musca domestica, Fannia* spec., *Stomoxys calcitrans, Hypoderma* spec., *Bibio hortulanus, Oscinella frit, Phorbia* spec., *Pegomyia hyoscyami, Calliphora erythrocephala, Lucilia* spec., *Chrysomyia* spec., *Ceratitis capitata, Dacus oleae* and *Tipula paludosa;* and from the order of the Siphonaptera, for example, *Xenopsylla cheopis.*

The active compounds according to the instant invention can be utilized, if desired, in the form of the usual formulations of compositions with conventional inert (i.e. plant compatible or herbicidally inert) pesticide diluents or extenders, i.e., diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as Freon; inert dispersible liquid diluent carriers, including inert organic solvents, such as aromatic hydrocarbons (e.g. benzene, toluene, xylene, alkyl naphthalenes, etc.) halogenated, especially chlorinated, aromatic hydrocarbons (e.g. chlorobenzenes, etc.), cycloalkanes, (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.) and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl ar polyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other insecticides, acaricides, nematocides, or fungicides, bactericides, rodenticides, herbicides, fetilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1-95% by weight, and preferably 0.5-90% by weight, of the mixture, whereas carrier composition mixtures suitable for direct application or field application generally contemplate those in which the active compound is present in an amount substantially between about 0.0001-10%, preferably 0.01-1%, by weight of the mixture. Thus, the present invention contemplates overall compositions which comprise mixtures of a conventional dispersible carrier vehicle such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001-95%, and preferably 0.01-95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50-100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20-100% by weight of the active compound.

When used against nematodes, the preparations are generally applied to an area of agriculture in amounts of 1 to 100 kg of active compound per hectare, and are then incorporated into the soil.

Furthermore, the present invention contemplates methods of selectively killing, combatting or controlling pests, e.g. insects, acarids and nematodes, which comprises applying to at least one of correspondingly (a) such insects, (b) such acarids, (c) such nematodes, and (d) the corresponding habitat thereof, i.e. the locus to be protected, e.g. to a growing crop, to an area where a crop is to be grown or to a domestic animal, a correspondingly combative or toxic amount, i.e. an insecticidally, acaricidally or nematocidally effective amount, of the particular active compound of the invention alone or together with a carrier vehicle as noted above. The instant formulations or compositions are applied in the usual manner, for instance by spraying, atomizing, vaporizing scattering, dusting, watering, squirting, sprinkling, pouring, fumigating, dressing, encrusting, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples:

EXAMPLE 1

Plutella test

Solvent: 3 parts by weight of acetone

Emulsifier: 1 part by weight of alkylaryl polyglycol ether

To produce a suitable preparation of active compound, 1 part by weight of the active compound was mixed with the stated amount of solvent containing the stated amount of emulsifier and the concentrate was diluted with water to the desired concentration.

Cabbage leaves (*Brassica oleracea*) were sprayed with the preparation of the active compound until dew moist and were then infested with caterpillars of the diamondback moth (*Plutella maculipennis*).

After the specified periods of time, the degree of destruction was determined as a percentage: 100% means that all the caterpillars were killed whereas 0% means that none of the caterpillars were killed.

The active compounds, the concentrations of the active compounds, the evaluation times and the results can be seen from the following table:

Table 1
(Plutella test)

| Active compound | | Active compound concentration in % | Degree of destruction in % after 3 days |
|---|---|---|---|
| (D) (known) structure with $CH_3S$, $CH_3$, $O-P(OC_2H_5)_2$ (=S), N=C-CH_3 | | 0.1<br>0.01 | 100<br>0 |
| (C) (known) structure with $CH_3S$, $CH_3$, $O-P(OC_2H_5)_2$ (=O), N=C-CH_3 | | 0.1<br>0.01 | 100<br>0 |
| (E) (known) structure with $CH_3S$, $CH_3$, $O-P(=S)(OCH_3)(NH-C_3H_7\,iso)$, N=C-CH_3 | | 0.1 | 20 |
| (28) structure with Cl, $CH_3$, N, $O-P(=S)(OC_2H_5)(C_2H_5)$ | | 0.1<br>0.01 | 100<br>100 |
| (18) structure with Cl, $CH_3$, N, $O-P(=S)(OC_3H_7\,iso)(CH_3)$ | | 0.1<br>0.01 | 100<br>100 |
| (10) structure with $SCH_3$, Cl, $CH_3$, N, $O-P(=S)(OC_2H_5)_2$ | | 0.1<br>0.01 | 100<br>100 |
| (12) structure with $SCH_3$, Cl, $CH_3$, N, $O-P(=S)(CH_3)(OC_3H_7\,iso)$ | | 0.1<br>0.01 | 100<br>100 |
| (11) structure with $SCH_3$, Cl, $CH_3$, N, $O-P(=S)(OC_2H_5)(C_2H_5)$ | | 0.1<br>0.01 | 100<br>100 |

Table 1-continued
| Active compound | (Plutella test) Active compound concentration in % | Degree of destruction in % after 3 days |
|---|---|---|
| 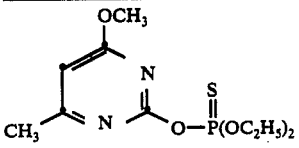 (30) | 0.1<br>0.01 | 100<br>100 |
| 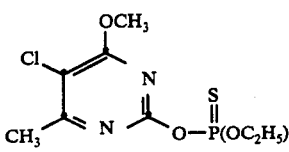 (31) | 0.1<br>0.01 | 100<br>100 |
| 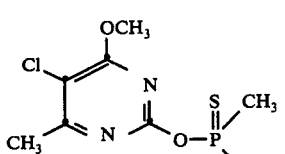 (25) | 0.1<br>0.01 | 100<br>100 |
| 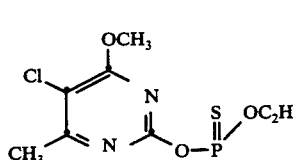 (16) | 0.1<br>0.01 | 100<br>100 |
| 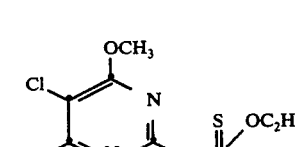 (23) | 0.1<br>0.01 | 100<br>100 |
| 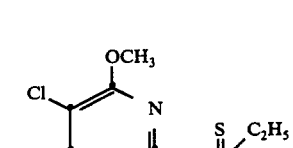 (15) | 0.1<br>0.01 | 100<br>100 |
| 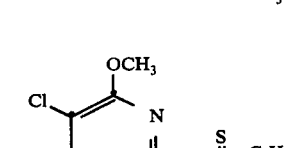 (22) | 0.1<br>0.01 | 100<br>100 |
| 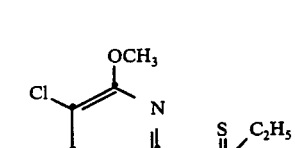 (32) | 0.1<br>0.01 | 100<br>100 |

Table 1-continued

| | (*Plutella* test) | |
|---|---|---|
| Active compound | Active compound concentration in % | Degree of destruction in % after 3 days |
| (24) | 0.1<br>0.01 | 100<br>100 |
| (26) | 0.1<br>0.01 | 100<br>100 |
| (3) | 0.1<br>0.01 | 100<br>100 |
| (8) | 0.1<br>0.01 | 100<br>100 |
| (5) | 0.1<br>0.01 | 100<br>100 |
| (4) | 0.1<br>0.01 | 100<br>95 |
| (7) | 0.1<br>0.01 | 100<br>100 |

EXAMPLE 2

Myzus test (contact action)

Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage plants (*Brassica oleracea*) which had been heavily infested with peach aphids (*Myzus persicae*) were sprayed with the preparation of the active compound until dripping wet.

After the specified periods of time, the degree of destruction was determined as a percentage: 100% means that all the aphids were killed whereas 0% means that none of the aphids were killed.

The active compounds, the concentrations of the active compounds, the evaluation times and the results can be seen from the following table:

Table 2 (*Myzus* test)

| Active compound | | Active compound concentration in % | Degree of destruction in % after 1 day |
|---|---|---|---|
| (structure: CH₃S–, CH₃–, with S=P(OCH₃)(NH–C₃H₇iso) group on pyrimidine) | (E) | 0.1<br>0.01<br>0.001 | 100<br>50<br>0 |
| (known) | | | |
| (structure: Cl, CH₃, pyrimidine with O–P(S)(OC₂H₅)(C₂H₅)) | (28) | 0.1<br>0.01<br>0.001 | 100<br>100<br>90 |
| (structure: SCH₃, CH₃, pyrimidine with O–P(S)(OC₂H₅)(C₂H₅)) | (17) | 0.1<br>0.01<br>0.001 | 100<br>99<br>90 |
| (structure: Cl, SCH₃, CH₃, pyrimidine with O–P(S)(OCH₃)₂) | (14) | 0.1<br>0.01<br>0.001 | 100<br>100<br>90 |
| (structure: Cl, SCH₃, CH₃, pyrimidine with O–P(S)(CH₃)(OC₃H₇iso)) | (12) | 0.1<br>0.01<br>0.001 | 100<br>99<br>40 |
| (structure: Cl, SCH₃, CH₃, pyrimidine with O–P(S)(OCH₃)(C₂H₅)) | (13) | 0.1<br>0.01<br>0.001 | 100<br>99<br>50 |
| (structure: Cl, SCH₃, CH₃, pyrimidine with O–P(S)(OC₂H₅)(C₂H₅)) | (11) | 0.1<br>0.01<br>0.001 | 100<br>100<br>99 |
| (structure: OCH₃, CH₃, pyrimidine with O–P(S)(OC₂H₅)₂) | (30) | 0.1<br>0.01<br>0.001 | 100<br>100<br>45 |

Table 2-continued (*Myzus* test)

| Active compound | | Active compound concentration in % | Degree of destruction in % after 1 day |
|---|---|---|---|
| (structure: Cl, OCH₃, CH₃, pyrimidine with O–P(S)(OC₂H₅)₂) | (31) | 0.1<br>0.01<br>0.001 | 100<br>100<br>99 |
| (structure: Cl, OCH₃, CH₃, pyrimidine with O–P(S)(OC₂H₅)(OC₃H₇)) | (23) | 0.1<br>0.01<br>0.001 | 100<br>100<br>99 |
| (structure: Cl, OCH₃, CH₃, pyrimidine with O–P(S)(C₂H₅)(OC₃H₇)) | (15) | 0.1<br>0.01<br>0.001 | 100<br>100<br>95 |
| (structure: Cl, OCH₃, CH₃, pyrimidine with O–P(S)(C₂H₅)(OCH₃)) | (22) | 0.1<br>0.01<br>0.001 | 100<br>100<br>70 |
| (structure: Cl, OCH₃, CH₃, pyrimidine with O–P(S)(C₂H₅)(OC₂H₅)) | (32) | 0.1<br>0.01<br>0.001 | 100<br>100<br>99 |
| (structure: CO–OC₃H₇iso, (CH₃)₃C, pyrimidine with O–P(S)(OC₂H₅)(C₂H₅)) | (6) | 0.1<br>0.01<br>0.001 | 100<br>100<br>99 |

EXAMPLE 3

Critical concentration test/soil insects

Test insect: *Phorbia antiqua* grubs in the soil
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was practically imaterial, the only decisive factor being the amount by weight of active compound per unit volume of soil, which is quoted in ppm (= mg/l). The soil was filled into pots and the pots were left to stand at room temperature.

After 24 hours the test insects were introduced into the treated soil and after a further 2 to 7 days the degree of effectiveness of the active compound was determined in % by counting the dead and live test insects. The degree of effectiveness was 100% if all test insects had been killed and was 0% if exactly as many test insects were still alive as in the case of the untreated control.

The active compounds, amounts used and results can be seen from the table which follows:

Table 3

(Soil insecticide test/*Phorbia antiqua* grubs in the soil)

| Active compound | | Degree of destruction in % at an active compound concentration of 5 ppm |
|---|---|---|
| (known) structure | (B) | 0 |
| (known) structure | (A) | 0 |
| (known) structure | (D) | 0 |
| (known) structure | (C) | 0 |
| (known) structure | (E) | 0 |
| structure | (27) | 100 |
| structure | (30) | 100 |
| structure | (31) | 100 |
| structure | (21) | 100 |
| structure | (22) | 100 |
| structure | (23) | 100 |
| structure | (24) | 100 |
| structure | (25) | 100 |
| structure | (10) | 100 |
| structure | (11) | 100 |

Table 3-continued
(Soil insecticide test/*Phorbia antiqua* grubs in the soil)

| Active compound | | Degree of destruction in % at an active compound concentration of 5 ppm |
|---|---|---|
| Cl–C(SCH₃)=C(N=)–C(CH₃)=N–O–P(=S)(CH₃)(OC₃H₇-iso) | (12) | 100 |
| Cl–C(SCH₃)=C(N=)–C(CH₃)=N–O–P(=S)(OCH₃)(C₂H₅) | (13) | 100 |
| Cl–C(SCH₃)=C(N=)–C(CH₃)=N–O–P(=S)(OCH₃)₂ | (14) | 100 |
| Cl–C(OCH₃)=C(N=)–C(CH₃)=N–O–P(=S)(C₂H₅)(OC₃H₇) | (15) | 100 |
| CH₃–C(=N)–CH=C(SCH₃)–N=C–O–P(=S)(OC₂H₅)₂ | (2) | 100 |
| CH₃–C(=N)–CH=C(SCH₃)–N=C–O–P(=S)(OC₂H₅)(C₂H₅) | (17) | 100 |
| (CH₃)₃C–C(=N)–CH=C(CO–OC₃H₇-iso)–N=C–O–P(=S)(OC₂H₅)₂ | (5) | 100 |
| Cl–C(OCH₃)=C(N=)–C(CH₃)=N–O–P(=S)(C₂H₅)(OC₂H₅) | (32) | 100 |

EXAMPLE 4

Critical concentration test/soil insects

Test insect: *Tenebrio moliton* larvae in the soil
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was practically immaterial, the only decisive factor being the amount by weight of active compound per unit volume of soil, which is quoted in ppm (= mg/l). The soil was filled into pots and the pots were left to stand at room temperature.

After 24 hours the test insects were introduced into the treated soil and after a further 2 to 7 days the degree of effectiveness of the active compound was determined in % by couting the dead and live test insects. The degree of effectiveness was 100% if all test insects had been killed and was 0% if exactly as many test insects were still alive as in the case of the untreated control.

The active compounds, amounts used and results can be seen from the table which follows:

Table 4
(Soil insecticide test/ *Tenebrio molitor* larvae in the soil)

| Active compound | | Degree of destruction in % at an active compound concentration of 5 ppm |
|---|---|---|
| pyrimidine–O–P(=S)(OC₂H₅)₂ (known) | (B) | 0 |
| pyrimidine–O–P(=S)(OCH₃)₂ (known) | (A) | 0 |
| CH₃–, SCH₃–, CH₃– substituted pyrimidine–O–P(=S)(OC₂H₅)₂ (known) | (D) | 0 |
| CH₃–, SCH₃–, CH₃– substituted pyrimidine–O–P(=O)(OC₂H₅)₂ (known) | (C) | 0 |

Table 4-continued (Soil insecticide test/ *Tenebrio molitor* larvae in the soil)

| Active compound | | Degree of destruction in % at an active compound concentration of 5 ppm |
|---|---|---|
| [structure with SCH₃, CH₃, pyrimidine, O-P(S)(OCH₃)(NHC₃H₇-iso)] (known) | (E) | 0 |
| [structure with Cl, OCH₃, CH₃, pyrimidine, O-P(S)(C₂H₅)(OCH₃)] | (22) | 100 |
| [structure with Cl, OCH₃, CH₃, pyrimidine, O-P(S)(OC₂H₅)(OC₃H₇)] | (23) | 100 |
| [structure with Cl, OCH₃, CH₃, pyrimidine, O-P(S)(OC₂H₅)(phenyl)] | (24) | 100 |
| [structure with Cl, OCH₃, CH₃, pyrimidine, O-P(S)(CH₃)(OC₃H₇-iso)] | (25) | 100 |
| [structure with CO-OC₃H₇-iso, (CH₃)₃C, pyrimidine, O-P(S)(OC₂H₅)₂] | (5) | 100 |

EXAMPLE 5

LT$_{100}$ test for Diptera

Test insect: *Aëdes aegypti*

Solvent: Acetone 2 parts by weight of active compound were dissloved in 1,000 parts by volume of solvent. The solution so obtained was diluted with further solvent to the desired lower concentrations.

2.5 ml of the solution of active compound were pipetted into a Petri dish. On the bottom of the Petri dish there was a filter paper with a diameter of about 9.5 cm. The Petri dish remained uncovered until the solvent had completely evaporated. The amount of active compound per m² of filter paper varied with the concentration of the solution of active compound. About 25 test insects were then placed in the Petri dish and it was covered with a glass lid.

The condition of the test insects was continuously observed. The time which was necessary for 100% destruction was determined.

The test insects, the active compounds, the concentrations of the active compounds and the times at which there was 100% destruction can be seen from the following table:

Table 5

(LT$_{100}$ test for *Diptera/Aëdes aegypti*)

| Active compound | | Active compound concentration of the solution in % | LT$_{100}$ in minutes (') |
|---|---|---|---|
| [structure with SCH₃, CH₃, pyrimidine with CH₃, O-P(S)(OC₂H₅)₂] (known) | (D) | 0.2<br>0.02<br>0.002 | 120'<br>180'<br>180' = 0% |
| [structure with SCH₃, CH₃, pyrimidine with CH₃, O-P(O)(OC₂H₅)₂] (known) | (C) | 0.2<br>0.02 | 60'<br>180' = 0% |

Table 5-continued
|  | (LT$_{100}$ test for *Diptera/Aedes aegypti*) | |
|---|---|---|
| Active compound | Active compound concentration of the solution in % | LT$_{100}$ in minutes (') |
| 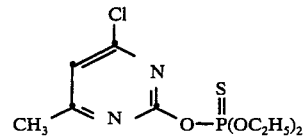 (27) | 0.2<br>0.02<br>0.002 | 60 '<br>60 '<br>180 ' |
| 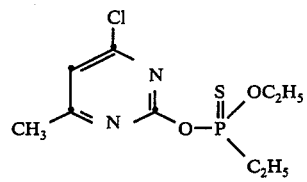 (28) | 0.2<br>0.02<br>0.002 | 60 '<br>60 '<br>180 ' |
| 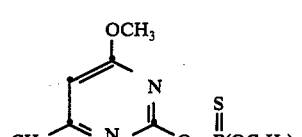 (30) | 0.2<br>0.02 | 60 '<br>120 ' |
| 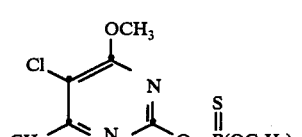 (31) | 0.2<br>0.02<br>0.002 | 60 '<br>120 '<br>180 ' = 80% |
| 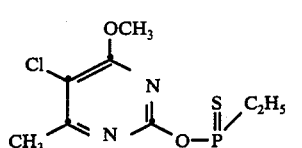 (32) | 0.2<br>0.02<br>0.002 | 60 '<br>120 '<br>180 ' = 90% |
| 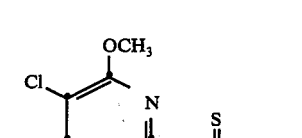 (21) | 0.2<br>0.02<br>0.002 | 60 '<br>120 '<br>180 ' = 80% |
| 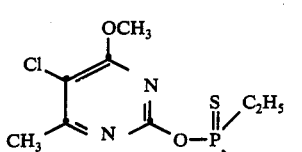 (22) | 0.2<br>0.02<br>0.002 | 60 '<br>120 '<br>180 ' = 90% |
| 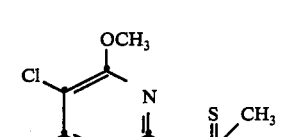 (25) | 0.2<br>0.02<br>0.002 | 60 '<br>120 '<br>180 ' |

Table 5-continued

(LT₁₀₀ test for *Diptera/Aedes aegypti*)

| Active compound | Active compound concentration of the solution in % | LT₁₀₀ in minutes (') |
|---|---|---|
| Compound (15): Cl, OCH₃, CH₃, N, O–P(S)(C₂H₅)(OC₃H₇) structure | 0.2<br>0.02<br>0.002 | 60'<br>120'<br>180' = 80% |
| Compound (2): SCH₃, CH₃, N, O–P(S)(OC₂H₅)₂ structure | 0.2<br>0.02<br>0.002 | 60'<br>120'<br>180' = 60% |
| Compound (26): CO–OCH₃, (CH₃)₃C, N, O–P(S)(OC₂H₅)₂ structure | 0.2<br>0.02<br>0.002 | 60'<br>120'<br>180' = 70% |
| Compound (5): CO–OC₃H₇iso, (CH₃)₃C, N, O–P(S)(OC₂H₅)₂ structure | 0.2<br>0.02<br>0.002 | 60'<br>120'<br>180' = 50% |
| Compound (60): CO–OC₃H₇iso, (CH₃)₃C, N, O–P(S)(OC₂H₅)(C₂H₅) structure | 0.2<br>0.02<br>0.002 | 60'<br>120'<br>180' = 50% |

EXAMPLE 6

Tetranychus test (resistant)

Solvent: 3 parts by weight or acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Bean plants (*Phaseolus vulgaris*), which had a height of approximately 10–30 cm, were sprayed with the preparation of the active compound until dripping wet. These bean plants were heavily infested with the two-spotted spider mite (*Tetranychus urticae*) in all stages of development.

After the specified periods of time, the degree of destruction was determined as a percentage: 100% means that all the spider mites were killed whereas 0% means that none of the spider mites were killed.

The active compounds, the concentrations of the active compounds, the evaluation times and the results can be seen from the following table:

Table 6

(*Tetranychus* test)

| Active compound | Active compound concentration in % | Degree of destruction in % after 2 days |
|---|---|---|
| (D) (known): CH₃S, CH₃, N, O–P(S)(OC₂H₅)₂, CH₃ structure | 0.1 | 0 |
| (C) (known): CH₃S, CH₃, N, O–P(O)(OC₂H₅)₂, CH₃ structure | 0.1 | 0 |

Table 6-continued (*Tetranychus* test)

| Active compound | | Active compound concentration in % | Degree of destruction in % after 2 days |
|---|---|---|---|
| [structure with CH₃S, NH-C₃H₇iso, P(=O)(OCH₃), CH₃, N] (known) | (E) | 0.1 | 0 |
| [structure with OCH₃, CH₃, N, O-P(=S)(OC₂H₅)₂] | (30) | 0.1 | 99 |
| [structure with OCH₃, Cl, CH₃, N, O-P(=S)(OC₂H₅)₂] | (31) | 0.1 | 100 |
| [structure with OCH₃, Cl, CH₃, N, O-P(=S)(CH₃)(OC₃H₇iso)] | (25) | 0.1 | 99 |
| [structure with OCH₃, Cl, CH₃, N, O-P(=S)(C₂H₅)(OC₃H₇)] | (15) | 0.1 | 100 |
| [structure with OCH₃, Cl, CH₃, N, O-P(=S)(C₂H₅)(OCH₃)] | (22) | 0.1 | 100 |
| [structure with OCH₃, Cl, CH₃, N, O-P(=S)(C₂H₅)(OC₂H₅)] | (32) | 0.1 | 100 |
| [structure with CO-OCH₃, (CH₃)₃C, N, O-P(=S)(OC₂H₅)₂] | (26) | 0.1 | 98 |
| [structure with CO-OC₂H₅, (CH₃)₃C, N, O-P(=S)(OC₂H₅)₂] | (3) | 0.1 | 100 |

Table 6-continued (*Tetranychus* test)

| Active compound | | Active compound concentration in % | Degree of destruction in % after 2 days |
|---|---|---|---|
| [structure with CO-OC₂H₅, (CH₃)₃C, N, O-P(=S)(OC₂H₅)(SC₃H₇)] | (8) | 0.1 | 90 |
| [structure with CO-OC₃H₇iso, (CH₃)₃C, N, O-P(=O)(OC₂H₅)₂] | (5) | 0.1 | 90 |
| [structure with CO-OC₃H₇iso, (CH₃)₃C, N, O-P(=S)(OC₂H₅)(C₂H₅)] | (6) | 0.1 | 99 |

EXAMPLE 7

Critical concentration test/nematodes

Test nematode: *Meloidogyne incognita*
Solvent: 3 parts by weight or acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with soil which was heavily infested with the test nematodes. The concentration of the active compound in the preparation was of practically no importance; only the amount of active compound per unit volume of soil, which is given in ppm, was decisive. The treated soil was filled into pots, lettuce was sown in and the pots were kept at a greenhouse temperature of 27° C.

After 4 weeks, the lettuce roots were examined for infestation with nematodes (root galls), and the degree of effectiveness of the active compound was determined as a percentage. The degree of effectiveness was 100% when infestation was completely avoided; it was 0% when the infestation was exactly the same as in the case of the control plants in untreated soil which had been infested in the same manner.

The active compounds, the amounts applied and the results can be seen from the following table:

Table 7

(Nematicide test/*Meloidogyne* spec.)

| Active compound | | Degree of destruction in % at an active compound concentration of 20 ppm |
|---|---|---|
| (known) structure B | (B) | 0 |
| (known) structure A | (A) | 0 |
| (known) structure D | (D) | 0 |
| (known) structure C | (C) | 0 |
| (known) structure E | (E) | 0 |
| Compound (31) | (31) | 100 |
| Compound (32) | (32) | 100 |
| Compound (20) | (20) | 100 |
| Compound (21) | (21) | 100 |
| Compound (22) | (22) | 100 |
| Compound (25) | (25) | 100 |
| Compound (11) | (11) | 100 |

EXAMPLE 8

Test with parasitic fly larvae/*Lucilia cuprina*

Solvent: 35 parts by weight of ethylene polyglycol monomethyl ether 35 parts by weight of nonylphenol polyglycol ether To produce a suitable preparation of active compound, 30 parts by weight of the active substance in question were mixed with the stated amount of solvent which contained the above-mentioned proportion of emulsifier and the concentrate thus obtained was diluted with water to the desired concentration.

About 20 fly larvae (Lucilia cuprina) were introduced into a test tube which contained approx. 2 cm³ of horse muscle. 0.5 ml of the preparation of active compound was applied to this horse meat. After 24 hours, the degree of destruction in % was determined. 100% means that all of the larvae had been killed and 0% means that no larvae had been killed.

The active compounds investigated, the concentrations of the active compounds used and the results obtained can be seen from the table which follows:

Table 8

(Test with parasitic fly larvae/*Lucilia cuprina*)

| Active compound | Active compound concentration in ppm | Degree of destruction in % |
|---|---|---|
| 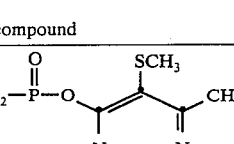 (known) (C) | 300<br>30<br>3 | 100<br>100<br><50 |
| 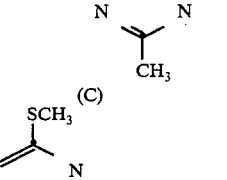 (10) | 100<br>30<br>10<br>3<br>1 | 100<br>100<br>100<br>100<br>>50 |

The 2-hydroxy-4-alkyl-pyrimidine derivatives (III) used as starting materials could be prepared, for example, in the manner described below:

EXAMPLE 9

(a) (CH₃)₃C—CO—CH₂—CO—CO—OC₂H₅

A mixture of 292 g (2 moles) of oxalic acid diethyl ester and 200 g (2 moles) of pinacoline was added dropwise to a solution of 224 g (2 moles) of potassium tert.-butylate in 300 ml of ethanol at 20°-30° C. The reaction mixture was stirred for 5 hours at 60°-70° C and was then cooled, and poured into 1 l of water. The aqueous solution was extracted once with 300 ml of methylene chloride, which was discarded. The aqueous phase was then acidified with concentrated hydrochloric acid while cooling with ice and extracted by shaking twice with 300 ml of toluene at a time, and the organic phase was separated off. It was dried over sodium sulfate, the solvent was stripped off in vacuo and the residue was distilled. 257 g (64% of theory) of a yellow oil of boiling point 80° C/2 mm Hg and having a refractive index $n_D^{23}$ of 1.4665 were obtained.

The following were synthesized analogously:

(b) (CH₃)₃C—CO—CH₂—CO—CO—OCH₃ (45% of theory; boiling point 95° C/ 4 mm Hg; $n_D^{25}$: 1.473) (c) (CH₃)₃C—CO—CH₂—CO—CO—OC₃H₇—iso (56% of theory; boiling point 95° C/2 mm Hg $n_D^{22}$: 1.4629)

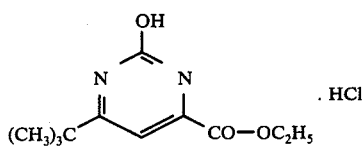 (d)

. HCl

A solution of 200 g (1 mole) of the compound described under (a) and 75 g (1.25 moles) of urea in 700 ml of ethanol and 100 ml of concentrated hydrochloric acid was heated for 10 hours under reflux. It was then cooled to −10° C and 1 l of ether was added. A precipitate formed, which was filtered off and dried. Thereafter, the precipitate was heated for 2 hours under reflux in 300 ml of ethanol which was saturated with hydrochloric acid gas. The mixture was then concentrated and the oily residue was caused to crystallize by means of ether. 54 g (21% of theory) of 2-hydroxy-6-carbethoxy-4-tert.-butyl-pyrimidine hydrochloride were obtained in the form of colorless crystals of melting point about 140° C (with decomposition).

The following were prepared analogously:

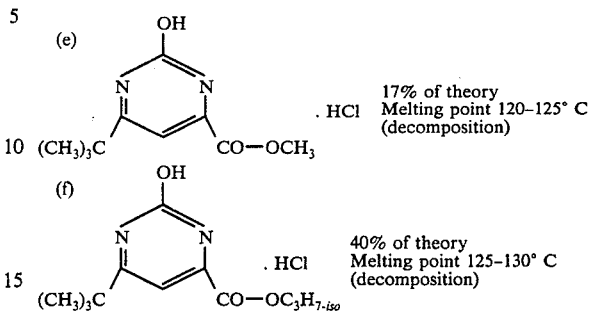

(e) . HCl  17% of theory  Melting point 120-125° C (decomposition)

(f) . HCl  40% of theory  Melting point 125-130° C (decomposition)

EXAMPLE 10

(a) 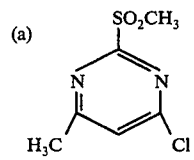

1.9 l of sodium hypochlorite (about 150 g of active chlorine per liter) were added slowly to a solution of 175 g (1 mole) of 2-methylmercapto-4-methyl-6-chloropyrimidine in 375 ml of concentrated hydrochloric acid and 375 ml of water at 5° C. The product which had precipitated was then filtered off and rinsed with water. This gave 170 g (82% of theory) of 2-methylsulfonyl-4-methyl-6-chloropyrimidine in the formn of colorless crystals of melting point 72° C.

(b) 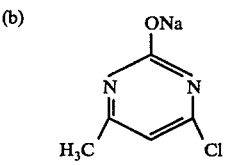

A solution of 41.3 g of (0.2 mole) of 2-methylsulfonyl4-methyl-6-chloropyrimidine in 80 ml of acetone was added dropwise at 0°-5° C to a solution of 28 g (0.5 mole) of potassium hydroxide in 150 ml of water. The mixture was stirred further, while cooling, until it was clear and was then stirred into 200 ml of saturated sodium chloride solution. The sodium salt which had precipitated was filtered off and 28.4 g (85% of theory) of the sodium salt of 2-hydroxy4-methyl-6-chloropyrimidine were thus obtained in the form of a pale yellow powder of melting point above 300° C.

(c) The compound of the formula

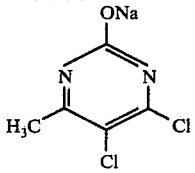

could be prepared analogously in 90% yield, and with melting point >300° C.

EXAMPLE 11

(a)
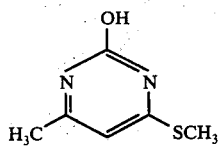

A mixture of 116 g (0.7 mole) of the sodium salt of 2-hydroxy-4-methyl-6-chloropyrimidine, 750 ml of dimethylformamide and 77 g (1.1 moles) of sodium methyl mercaptide was stirred for 1 - 2 hours at 100° C. It was then cooled to room temperature, 500 ml of ether were added and the product which has precipitated was filtered off. The filter residue was suspended in 300 ml of water and brought to pH 6 by addition of concentrated hydrochloric acid. The product was then again filtered off and rinsed with a little water. This gave 55 g (47% of theory) of 2-hydroxy-4-methyl-6-methylmercaptopyrimidine in the form of colorless crystals of melting point 165° C.

The following could be prepared analogously:

(b)
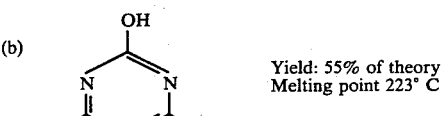
Yield: 55% of theory
Melting point 223° C (c)
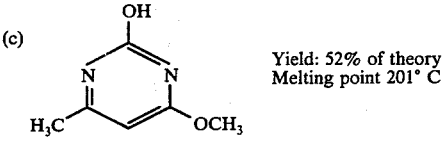
Yield: 52% of theory
Melting point 201° C (d)
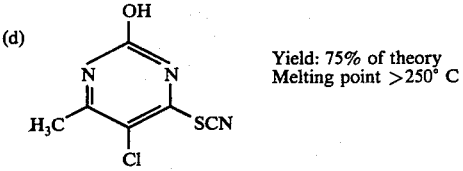
Yield: 75% of theory
Melting point >250° C

EXAMPLE 12

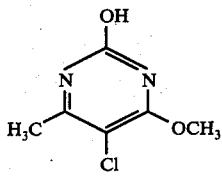

Hydrogen chloride gas was passed into a suspension of 80.4 g (0.4 mole) of the sodium salt of 2-hydroxy-4-methyl-5,6-dichloropyrimidine in 600 ml of methanol until the mixture reacted strongly acid. The mixture was then stirred for a further hour and thereafter the solvent was distilled off in vacuo. The residue was triturated with 50 ml of water and filtered off. 41.3 g (59% of theory) of 2-hydroxy-4-methyl-5-chloro-6-methoxypyrimidine were obtained in the form of a beige powder of melting point 235° C.

These intermediates are used in the process of this invention as illustrated by the following preparative Examples:

EXAMPLE 13

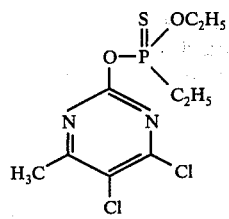 (1)

A mixture of 27 g (0.11 mole) of sodium salt of 2-hydroxy-4-methyl-5,6-dichloropyrimidine (Example 10c), 13.8 g (0.1 mole) of potassium carbonate, 150 ml of acetonitrile and 17.2 g (0.1 mole) of O-ethyl-ethanethionophosphonic acid ester chloride was stirred for 8 hours at 55°-60° C. It was then cooled to room temperature, 400 ml of toluene were added and the organic phase was washed 3 times with 200 ml of water at a time. The toluene solution was dried over sodium sulfate and the solvent was then distilled off in vacuo. The residue was subjected to slight distillation and 18.1 g (57% of theory) of O-ethyl-O-[5,6-dichloro-4-methylpryimidin(2)yl]-thionoethanephosphonic acid ester were obtained in the form of a yellow oil having a refractive index $n_D^{20}$ of 1.5466.

EXAMPLE 14

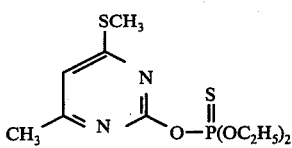 (2)

A mixture of 15.6 g (0.1 mole) of 2-hydroxy-4-methyl-6-methyl-mercaptopyrimidine (Example 11a), 20.7 g (0.15 mole) of potassium carbonate, 200 ml of acetonitrile and 18.9 g of O,O-diethylthionophosphoric acid diester chloride was stirred for 7 hours at 50° C. After cooling to room temperature, 400 ml of toluene were added and the mixture was washed 3 times with 200 ml of water at a time. The organic phase was then dried over sodium sulfate and the solvent was stripped off in vacuo. The residue was subjected to slight distillation and 22.4 g (73% of theory) of O,O-diethyl-O-[4-methyl-6-methyl-mercaptopyrimidin-(2)-yl]-thionophosphoric acid ester were obtained in the form of a brown oil of refractive index $n_D^{24}$: 1.5350.

EXAMPLE 15

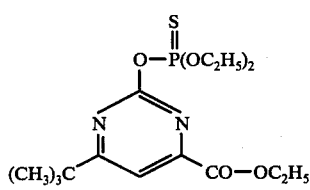 (3)

18.8 g (0.1 mole) of O,O-diethyl-thionophosphoric acid ester diester chloride (Example 9d) were added dropwise to a suspension of 26 g (0.1 mole) of 2-hydroxy-6-carbethoxy-4-tert.-butylpyrimidine hydrochloride and 29.2 g (0.21 moles) of potassium carbonate in 200 ml of acetonitrile. The reaction mixture was stirred for 30 hours at 40° C and then poured into 500 ml of toluene. This mixture was extracted by shaking twice with 500 ml of water at a time and the organic phase was separated off and dried over sodium sulfate. The solvent was then stripped off and the residue was subjected to slight distillation at 100° C. 22.2 g (59% of theory) of O,O-diethyl-O-[4-tert.-butyl(-6-carbethoxy-pyrimidin(2)yl]-thionophosphoric acid ester were obtained in the form of a yellow oil having a refractive index $n_D^{25}$ of 1.4970.

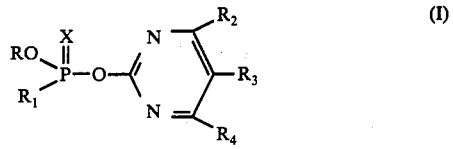

could each be prepared by analogous methods:

Table 9

| Compound No. | X | R | $R_1$ | $R_2$ | $R_3$ | $R_4$ | Yield (% of theory) | Physical data (refractive index; melting point, °C |
|---|---|---|---|---|---|---|---|---|
| 4 | O | $-C_2H_5$ | $-OC_2H_5$ | $(CH_3)_3C-$ | H | $-CO-OC_3H_7$- iso | 51 | $n_D^{24}$:1.4648 |
| 5 | S | $-C_2H_5$ | $-OC_2H_5$ | $(CH_3)_3C-$ | H | $-CO-OC_3H_7$- iso | 44 | $n_D^{24}$:1.4938 |
| 6 | S | $-C_2H_5$ | $-C_2H_5$ | $(CH_3)_3C-$ | H | $-CO-OC_3H_7$- iso | 56 | $n_D^{24}$:1.5022 |
| 7 | O | $-C_2H_5$ | $-OC_2H_5$ | $(CH_3)_3C-$ | H | $-CO-OC_2H_5$ | 67 | $n_D^{24}$:1.4890 |
| 8 | S | $-C_2H_5$ | $-SC_3H_7$- n | $(CH_3)_3C-$ | H | $-CO-OC_2H_5$ | 47 | $n_D^{24}$:1.5258 |
| 9 | S | $-C_2H_5$ | —C₆H₅ | $(CH_3)_3C-$ | H | $-CO-OC_2H_5$ | 71 | $n_D^{25}$:1.5800 |
| 10 | S | $-C_2H_5$ | $-OC_2H_5$ | $CH_3-$ | Cl | $-SCH_3$ | 73 | $n_D^{25}$:1.5420 |
| 11 | S | $-C_2H_5$ | $-C_2H_5$ | $CH_3-$ | Cl | $-SCH_3$ | 76 | $n_D^{25}$:1.5600 |
| 12 | S | $-C_3H_7$- iso | $-CH_3$ | $CH_3-$ | Cl | $-SCH_3$ | 77 | 61 |
| 13 | S | $-CH_3$ | $-C_2H_5$ | $CH_3-$ | Cl | $-SCH_3$ | 77 | $n_D^{24}$:1.5748 |
| 14 | S | $-CH_3$ | $-OCH_3$ | $CH_3-$ | Cl | $-SCH_3$ | 45 | 72 |
| 15 | S | $-C_3H_7$- n | $-C_2H_5$ | $CH_3-$ | Cl | $-OCH_3$ | 62 | $n_D^{24}$:1.5229 |
| 16 | S | $-C_2H_5$ | $-SC_3H_7$- n | $CH_3-$ | Cl | $-OCH_3$ | 37 | $n_D^{24}$:1.5412 |
| 17 | S | $-C_2H_5$ | $-C_2H_5$ | $CH_3-$ | H | $-SCH_3$ | 67 | $n_D^{24}$:1.5559 |
| 18 | S | $-C_3H_7$- iso | $-CH_3$ | $CH_3-$ | H | Cl | 75 | $n_D^{24}$:1.5268 |
| 19 | O | $-C_2H_5$ | $-OC_2H_5$ | $CH_3-$ | Cl | Cl | 67 | $n_D^{26}$:1.4832 |
| 20 | S | $-C_2H_5$ | $-C_2H_5$ | $CH_3-$ | Cl | $-SCN$ | 48 | $n_D^{24}$:1.5863 |
| 21 | S | $-CH_3$ | $-OCH_3$ | $CH_3-$ | Cl | $-OCH_3$ | 27 | $n_D^{25}$:1.5295 |
| 22 | S | $-CH_3$ | $-C_2H_5$ | $CH_3-$ | Cl | $-OCH_3$ | 51 | $n_D^{25}$:1.5373 |
| 23 | S | $-C_3H_7$- n | $-OC_2H_5$ | $CH_3-$ | Cl | $-OCH_3$ | 50 | $n_D^{25}$:1.5145 |
| 24 | S | $-C_2H_5$ | —C₆H₅ | $CH_3-$ | Cl | $-OCH_3$ | 61 | $n_D^{25}$:1.5770 |
| 25 | S | $-C_3H_7$- iso | $-CH_3$ | $CH_3-$ | Cl | $-OCH_3$ | 31 | 69 |
| 26 | S | $-C_2H_5$ | $-OC_2H_5$ | $(CH_3)_3C-$ | H | $-CO-OCH_3$ | 28 | $n_D^{24}$:1.4995 |
| 27 | S | $-C_2H_5$ | $-OC_2H_5$ | $CH_3-$ | H | Cl | 37 | $n_D^{25}$:1.5132 |
| 28 | S | $-C_2H_5$ | $-C_2H_5$ | $CH_3-$ | H | Cl | 75 | $n_D^{25}$:1.5288 |
| 29 | S | $-C_2H_5$ | $-OC_2H_5$ | $CH_3-$ | Cl | Cl | 33 | $n_D^{25}$:1.5425 |
| 30 | S | $-C_2H_5$ | $-OC_2H_5$ | $CH_3-$ | H | $-OCH_3$ | 46 | $n_D^{24}$:1.5040 |
| 31 | S | $-C_2H_5$ | $-OC_2H_5$ | $CH_3-$ | Cl | $-OCH_3$ | 39 | $n_D^{24}$:1.5185 |
| 32 | S | $-C_2H_5$ | $-C_2H_5$ | $CH_3-$ | Cl | $-OCH_3$ | 63 | $n_D^{25}$:1.5312 |
| 33 | S | $-C_2H_5$ | —C₆H₅ | $CH_3-$ | Cl | Cl | 61 | $n_D^{25}$:1.5870 |
| 34 | S | $-C_3H_7$- n | $-OC_2H_5$ | $CH_3-$ | Cl | Cl | 78 | $n_D^{25}$:1.5130 |

The following compounds of the formula

Other compounds which can be similarly prepared include:

Table 10

| Compound No. | X | R | $R_1$ | $R_2$ | $R_3$ | $R_4$ |
|---|---|---|---|---|---|---|
| 35 | S | $-C_4H_9$- n | $-C_4H_9$- n | $CH_3-$ | H | Br |
| 36 | S | $-C_4H_9$- s | $-C_4H_9$- s | $C_2H_5-$ | H | Br |
| 37 | S | $-C_4H_9$- i | $-C_4H_9$- i | $CH_3-$ | Cl | Br |
| 38 | S | $-C_4H_9$- t | $-C_4H_9$- t | $C_2H_5-$ | Cl | Br |
| 39 | S | $-C_2H_5$ | $-C_3H_7$-n | $CH_3-$ | Br | $-OCH_3$ |
| 40 | S | $-C_2H_5$ | $-C_3H_7$- iso | $CH_3-$ | Br | $-SCH_3$ |
| 41 | S | $-C_2H_5$ | $-OC_3H_7$- n | $CH_3-$ | Br | Br |
| 42 | S | $-C_2H_5$ | $-OC_3H_7$- iso | $CH_3-$ | H | $-COOCH_3$ |
| 43 | S | $-C_2H_5$ | $-O-C_4H_9$- n | $CH_3-$ | H | $-COOC_2H_5$ |
| 44 | S | $-C_2H_5$ | $-O-C_4H_9$- s | $CH_3-$ | H | $-COOC_3H_7$- iso |
| 45 | S | $-C_2H_5$ | $-O-C_4H_9$- i | $C_4H_9$- t- | Cl | $-COOCH_3$ |
| 46 | S | $-C_2H_5$ | $-O-C_4H_9$- t | $C_4H_9$- t- | Br | $-COOCH_3$ |
| 47 | S | $-C_2H_5$ | $-SCH_3$ | $C_4H_9$- t- | Cl | $-COOC_2H_5$ |
| 48 | S | $-C_2H_5$ | $-SC_2H_5$ | $C_4H_9$- t- | Br | $-COOC_2H_5$ |
| 49 | S | $-C_2H_5$ | $-SC_3H_7$- n | $C_4H_9$- t- | Cl | $-COOC_3H_7$- iso |
| 50 | S | $-C_2H_5$ | $-SC_3H_7$- iso | $C_4H_9$- t- | Br | $-COOC_3H_7$- iso |
| 51 | S | $-C_2H_5$ | $S-C_4H_9$- n | $CH_3-$ | Cl | $-COOCH_3$ |
| 52 | S | $-C_2H_5$ | $S-C_4H_9$- s | $CH_3-$ | Br | $-COOCH_3$ |
| 53 | S | $-C_2H_5$ | $S-C_4H_9$- i | $CH_3-$ | Cl | $-COOC_2H_5$ |
| 54 | S | $-C_2H_5$ | $S-C_4H_9$- t | $CH_3-$ | Br | $-COOC_2H_5$ |
| 55 | S | $-C_2H_5$ | $OC_2H_5$ | $CH_3-$ | Cl | $-COOC_3H_7$- iso |
| 56 | S | $-C_2H_5$ | $OC_2H_5$ | $CH_3-$ | Br | $-COOC_3H_7$- iso |
| 57 | S | $-C_2H_5$ | $OC_2H_5$ | $CH_3-$ | H | $-OC_3H_7$- n |

Table 10-continued

| Compound No. | X | R | $R_1$ | $R_2$ | $R_3$ | $R_4$ |
|---|---|---|---|---|---|---|
| 58 | S | $-C_2H_5$ | $OC_2H_5$ | $CH_3-$ | H | $-SC_3H_7\text{-}n$ |
| 59 | S | $-C_2H_5$ | $OC_2H_5$ | $CH_3-$ | H | $-OC_2H_5$ |
| 60 | S | $-C_2H_5$ | $OC_2H_5$ | $CH_3-$ | H | $-SC_2H_5$ |

It will be appreciated that the instant specification and examples are set forth by way of illustration and not limitation, and that various modifications and changes may be made without departing from the spirit and scope of the present invention.

What is claimed is

1. An O-alkyl-O-[4-alkylpyrimdin(2)yl]-(thiono)-(thiol)phosphoric (phosphonic) acid ester of the formula

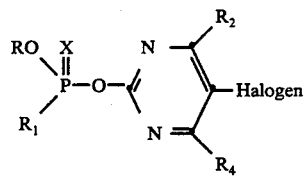

in which
R is alkyl with 1 to 9 carbon atoms,
$R_1$ is alkyl, alkoxy or alkylmercapto each with 1 to 6 carbon atoms, or phenyl
$R_2$ is alkyl with 1 to 6 carbon atoms,
$R_4$ is halogen, thiocyanato or alkoxy, alkylmercapto or alkoxycarbonyl with 1 to 4 carbon atoms in each alkyl radical, and
X is oxygen or sulfur.

2. A compound according to claim 1, in which R is straight-chain or branched alkyl with 1 to 4 carbon atoms, $R_1$ is alkyl, alkoxy or alkylmercapto each with 1 to 4 carbon atoms, or phenyl, $R_2$ is straight-chain or branched alkyl with 1 to 4 carbon atoms, halogen chlorine or bromine, and $R_4$ is chlorine, bromine or thiocyanato, or alkoxy, alkylmercapto or alkoxycarbonyl with 1 to 3 carbon atoms in each alkyl radical.

3. The compound according to claim 1, wherein such compound is O,O-diethyl-O-[4-methyl-5-chloro-6-methyl-mercaptopyrimidin(2)yl]-thionophosphoric acid ester of the formula

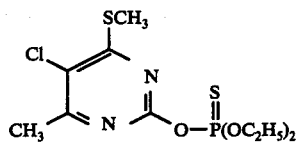

4. The compound according to claim 1, wherein such compound of O,O-dimethyl-O-[4-methyl-5-chloro-6-methoxy-pyrimidin(2)yl]-thionophosphoric acid ester of the formula

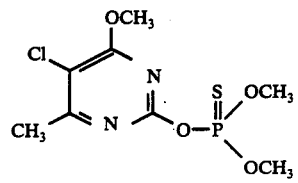

5. The compound according to claim 1, wherein such compound is O-methyl-O-[4-methyl-5-chloro-6-methoxy-pyrimidin (2)yl]-ethanethionophosphonic acid ester of the formula

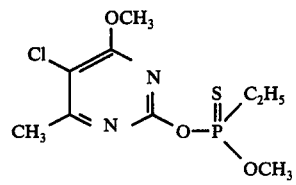

6. The compound according to claim 1, wherein such compound is O,O-diethyl-O-[4-methyl-5-chloro-6-methoxy-pyrimidin(2)yl]-thionophosphoric acid ester of the formula

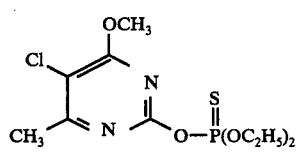

7. The compound according to claim 1, wherein such compound is O-ethyl-O-[4-methyl-5-chloro-6-methoxy-pyrimidin (2)yl]-ethanethionophosphonic acid ester of the formula

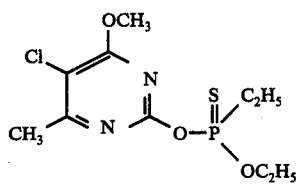

8. An insecticidal, acaricidal or nematocidal composition containing as active ingredient an isecticidally, acaricidally or nematocidally effective amount of a compound according to claim 1 in admixture with a diluent.

9. A method of combatting insects, acarids or nematodes which comprises applying to the insects, acarids, or nematodes, or to a habitat thereof, an insecticidally, acaricidally or nematocidally effective amount of a compound according to claim 1.

10. The method according to claim 9 in which said compound is
O,O-diethyl-O-[4-methyl-5-chloro-6-methyl-mercaptopyrimidin(2)yl]-thionophosphoric acid ester,
O,O-dimethyl-O-[4-methyl-5-chloro-6-methoxy-pyrimidin(2)yl]-thionophosphoric acid ester,
O-methyl-O-[4-methyl-5-chloro-6-methoxy-pyrimidin (2)yl]-ethanethionophosphonic acid ester,
O,O-diethyl-O-[4-methyl-5-chloro-6-methoxy-pyrimidin(2)yl]-thionophosphoric acid ester or
O-ethyl-O-[4-methyl-5-chloro-6-methoxy-pyrimidin (2)yl]-ethanethionophosphonic acid ester.

* * * * *

UNITED STATES PATENT AND TRADEMARK OFFICE
CERTIFICATE OF CORRECTION

PATENT NO. : 4,113,860
DATED : September 12, 1978
INVENTOR(S) : Fritz Maurer et al It is certified that error appears in the above-identified patent and that said Letters Patent are hereby corrected as shown below:

Column 37, line 55, Claim 4, cancel "of" and substitute therefor --is-- ;

Column 38, line 46, Claim 8, cancel "isecticidally" and substitute therefor --insecticidally-- .

Signed and Sealed this

Seventeenth Day of April 1979

[SEAL]

Attest:

RUTH C. MASON
Attesting Officer

DONALD W. BANNER
Commissioner of Patents and Trademarks